US005821249A

United States Patent [19]

Wood et al.

[11] Patent Number: 5,821,249
[45] Date of Patent: Oct. 13, 1998

[54] ANHYDROECOGONINE COMPOUNDS AND THEIR USE AS ANTICHOLINERGIC AGENTS

[75] Inventors: Ronald W. Wood, Nyack; Hassan A. N. El-Fawal, Middletown; John F. Graefe, Greenwood Lake, all of N.Y.; Lung C. Chen, Upper Saddle River, N.J.; Jalil Shojaie, Tuxedo, N.Y.

[73] Assignee: University of Rochester, Rochester, N.Y.

[21] Appl. No.: 706,105

[22] Filed: Aug. 30, 1996

Related U.S. Application Data

[62] Division of Ser. No. 76,315, Jun. 11, 1993, Pat. No. 5,552,407.

[51] Int. Cl.$^6$ .......................... C07D 213/20; A61K 31/44
[52] U.S. Cl. ............................ 514/291; 514/304; 546/91; 546/132
[58] Field of Search .................... 546/91, 132; 514/291, 514/304

[56] References Cited

U.S. PATENT DOCUMENTS 4,467,095  8/1984  Treves et al. ............................ 546/342

FOREIGN PATENT DOCUMENTS 0 445 731  9/1991  European Pat. Off. ............... 546/152

OTHER PUBLICATIONS

Boni et al., "Pyrolysis of Cocaine Free Base" *FASEB J.* 2(5) 1988, abstr. 4891.
Carroll et al., "Probes for the Cocaine Receptor. Potentially Irreversible Ligands for the Dopamine Transporter" *J. Med. Chem.* 35:1813–1817 (1992).
Cereda et al., "Synthesis and Biological Evaluation of New Antimuscarinic Compounds with Amidine Basic Centers. A Useful Bioisosteric Replacement of Classical Cationic Heads" *J. Med. Chem.* 33:2108–2113 (1990).
Davies, "Novel 2–substituted cocaine analogs: binding properties at dopamine transport sites in rat striatum" *Eur. J. Pharmacol.* 244:93–97 (1993).
Deckers, "The chemistry of new derivatives of tropane alkaloids and the pharmacokinetics of a new quarternary compound" *Postgrad, Med. J.* 51 (*Suppl.* 7):76–81 (1975).
El–Fawal et al., "The Biventer Cervicis Nerve–Muscle Preparation of Adult Hens: Effects of Phenyl Saligenin Phosphate Administration" *Neurotoxicology* 9:625–636 (1988).
Fishcman et al., "A Comparison of the Subjective and Cardiovascular Effects of Cocaine and Lidocaine in Humans" *Pharmacol. Biochem. Behav.* 18:123–127 (1983).
Foltin et al., "Demonstration of naturalistic methods for cocaine smoking by human volunteers" *Drug Alcohol Depend.* 26:145–154 (1990).

Gross, "Ipratropium Bromide" *New Eng. J. Med.* 319:486–494 (1988).
Inaba, "Cocaine: Pharmacokinetics and biotransformation in man" *Can. J. Physiol. Pharmacol.* 67:1154–1157 (1989).
Jacob III et al., "A Pyrolysis Product, Anhydroecgonine Methyl Ester (Methylecgonidine), is in the Urine of Cocaine Smokers" *J. Anal. Toxicol.* 14:353–357 (1990).
Leete, "Biosynthesis of the Pyrrolidine Rings of Cocaine and Cuscohygrine from [5–$^{14}$ C]Ornithine via a Symmetrical Intermediate" *J. Am. Checm. Soc.* 104:1403–1408 (1982).
Lowry et al., "Identification of Two Novel Cocaine Metabolites in Bile by Gas Chromatography and Gas Chromatography/Mass Spectrometry in a Case of Acute Intravenous Cocaine Overdose" *J. Anal. Toxicol.* 3:91–95 (1979).
Martin et al., "Pyrolysis and Volatilization of Cocaine" *J. Anal. Toxicol.* 13:158–162 (1989).
Meyer et al., "Effects of Benzoyltropine and Tropacocaine on Several Cholinergic Processes in the Rat Brain" *J. Pharmacol. Exp. Ther.* 254:584–590 (1988).
Orer et al., "Antagonism of Acetylcholine Action in Guinea–Pig Tracheal Smooth Muscle and Epithelium by Pirenzepine, 4–DAMP and Atropine" *Arch. Int. Pharmacodyn.* 305:45–54 (1990).
Sharkey et al., "Cocaine Inhibits Muscarinic Cholinergic Receptors in Heart and Brain" *J. Pharmacol. Exp. Ther.* 246:1048–1052 (1988).
Taylor et al., "Betel–nut chewing and asthma" *Lancet* 339:1134–1136 (1992).
Wise, et al., *Chemical Abstracts* vol. 51, No. 21; Abstract 16501e and h, Nov. 10, 1957.
Zaugg et al., *Chemical Abstracts* vol. 53, No. 1; Abstract 1327h, Jan. 10, 1959.
Zirkle, et al., *Chemical Abstracts* vol. 57, No. 3; Abstract 3390g, Aug. 6, 1962.

*Primary Examiner*—Zinna Northington Davis
*Attorney, Agent, or Firm*—Morrison & Foerster LLP

[57] ABSTRACT

Methylecgonidine (MEG; anhydroecgonine methylester), is produced when cocaine base ("crack") is heated. MEG alone and in combination with cocaine was tested for action on isolated tracheal rings stimulated to contact with acetylcholine. At micromolar concentrations, cocaine sensitized tracheal rings, increasing both the potency and efficacy of acetylcholine-induced contraction. Surprisingly, MEG, at nanomolar concentrations and above, non-competitively and irreversibly antagonized acetylcholine-induced contraction independently of the actions of cocaine. MEG also displayed antihistaminic activity. Therefore, MEG and anticholinergically active derivatives or analogues thereof are useful in the prevention or treatment of a disease or disorder treatable by an antimuscarinic anticholinergic agent, an anti-histaminic agent or a spasmolytic agent, in particular bronchoconstriction in a number of pulmonary diseases such as asthma.

18 Claims, 7 Drawing Sheets

ANHYDROECOGONINE COMPOUNDS AND THEIR USE AS ANTICHOLINERGIC AGENTS

This application is a divisional application of prior application Ser. No. 08/076,315 filed Jun. 11, 1993, now U.S. Pat. No. 5,552,407.

This invention was funded in part by a research grant from the National Institute on Drug Abuse, which provides to the United States Government certain rights in this invention.

BACKGROUND OF THE INVENTION

1. Field of the Invention

The present invention relates to the discovery of anticholinergic action of cocaine derivatives, in particular methylecgonidine (MEG), and methods of using this compound and its anticholinergically active derivatives in the treatment of pulmonary diseases associated with bronchoconstriction.

2. Description of the Background Art

A. CRACK COCAINE AND ITS PYROLYSIS PRODUCTS

"Crack" (cocaine base) is a drug with great abuse potential that when smoked can lead to a compulsive abuse disorder complicated by behavioral and physiological toxicity. When a flame is applied to crack, the drug volatilizes in significant amounts at temperatures only slightly below those at which pyrolysis occurs. As the temperature of the drug atmosphere cools the vapors condense, forming droplets that deposit in the airways. The first two pyrolysis products produced on heating are benzoic acid and anhydroecgonine methyl ester (methylecgonidine, MEG) (B. R. Martin et al., *J. Anal. Toxicol.* 13:158 (1989)). Benzoic acid is white, and sublimates. MEG is a clear liquid at room temperature. Although yellow and black pyrolysis products are commonly seen in drug paraphernalia, MEG predominates on a mass basis.

MEG has been detected in the urine of crack smokers, but not in users of cocaine taken by other routes (P. Jacob III et al., *J. Anal. Toxicol.* 14:353 (1990)). These authors suggested that MEG might be a cholinergic agonist, based on its structural similarity to arecoline and anatoxin A. However, the observations of the present inventors, disclosed herein, indicate that the opposite is in fact the case.

B. COCAINE AND CHOLINERGIC PHENOMENA

A number of observations link cocaine with cholinergic and bronchopulmonary events. Acetylcholine (ACh), a physiological and prototypical cholinergic agonist, produces constriction of the tracheobronchial musculature. Cocaine has been reported to sensitize tracheal rings to ACh, increasing either peak tension in the rat (Y. Gomi et al. *Nippon Yakurigaku Zasshi—Fol. Pharmacol. Jap.* 74:539 (1978)) or decreasing threshold in the guinea pig (Y. Gomi et al., *Yakugaku Zasshi—J. Pharmaceut. Soc. Jap.* 96:333 (1976)). Cocaine administration to asthmatic subjects aggravates the asthmatic condition (R. B. Rubin et al., *Am. J. Med.* 88:438 (1990); N. A. Ettinger et al., *Am. J. Med.* 87:664 (1989)). Crack smokers have suffered fatal bronchoconstriction (A. N. Rao et al., *NYS J. Med.* 90:511 (1990)). Betel nut, of which arecoline is the major alkaloid, aggravates asthma (K. S. Kiyingi, *PNG Med. J.* 34:117 (1991); R. F. H. Taylor et al., *Lancet* 339:1134 (1992)), and arecoline has consistent effects in vitro on tracheal ring contraction (Taylor et al., supra).

The role of cholinergic transmission in cocaine abuse was studied briefly twenty years ago, and has not been followed up to any extent. Cocaine itself has antimuscarinic effects, but only at concentrations higher than those associated with euphoria. Cocaine bears some structural resemblance to atropine, a prototypical anticholinergic drug, and related compounds.

C. DISEASES OF BRONCHOCONSTRICTION AND THEIR TREATMENT

For a detailed description of anticholinergic agents and their use in treating various diseases including respiratory diseases, see: Faye, W. P., PRINCIPLES OF MEDICINAL CHEMISTRY, Lea and Fibiger, 1989, pp. 328–348; Gilman, A. G. et al., (eds), *THE PHARMACOLOGICAL BASIS OF THERAPEUTICS*, 8th Edition, Macmillan Publishing Co., New York, 1990, chapter 8, pp. 150–165, both of which references are hereby incorporated by reference herein). A variety of drugs of different classes have found uses in diseases such as asthma and chronic pulmonary disease. These drugs include (1) β-adrenergic agonist bronchodilators, (2) the quaternary antimuscarinic n-isopropylatropine that inhibits acetylcholine-induced contraction of the tracheal musculature, (3) the phosphodiesterase inhibitor theophylline, (4) mast cell stabilizing agents such as the cromoglycates, (5) the antihistamines, and (6) steroids which reduce inflammatory responses to inhaled substances. See Gilman et al. (supra).

Current recommended practice for the treatment of asthma is to reduce the inflammatory and ronchoconstrictive response to allergens while judiciously using bronchodilators to provide symptomatic relief. Frequent routine use of β-adrenergic agonists by asthmatic patients has been correlated with increased symptoms, airway hyperresponsiveness and mortality. See: Page, C. E. et al., *Am. Rev. Respir. Dis.* 147:S29–S32 (1993).

The parasympathetic nervous system plays a major role in regulating bronchomotor tone. Largely owing to the introduction of the quaternary anticholinergic ipratropium bromide (Atrovent®) (gross, H. J., *New Eng. J. Med.* 319:486–494 (1988)), anticholinergic therapy of respiratory disease has been revived (Higgenbottam, T. W. et al., eds., *Postgrad. Med. J.* 63 (Suppl):1–93 (1987)). Ipratropium has little or no effect on the function of ciliated bronchial epithelium (Gross, supra). The muscarinic antagonists are particularly effective against bronchoconstriction caused by parasympathomimetic drugs, but only partially antagonize the bronchoconstriction induced by histamine, bradykinin or prostaglandin F2α. This action on the indirect bronchoconstrictive effects of inflammatory mediators that are released during asthma attacks forms the basis for the use of anticholinergics in treating reversible airway disease (Gross, supra). A major advantage of ipratropium is that elevated tissue concentrations can be achieved without systemic anticholinergic effects, due to lack of absorption. Another advantage is its duration of action, wherein the pharmacologic effect becomes maximal in about an hour, and persists for several hours.

There is clearly a need in the art for new agents with improved activity profiles and new methods for the treatment of pulmonary diseases associated with bronchoconstriction. The present invention is addressed in part to this need.

SUMMARY OF THE INVENTION

The present invention relates to compositions comprising methylecgonidine (MEG) or derivatives or analogues thereof having anticholinergic activity, methods of preventing of inhibiting cholinergic responses and methods of using the composition to prevent or treat a disease associated with bronchoconstriction.

Specifically, the present invention is directed to a composition useful for preventing or inhibiting bronchoconstriction in a subject comprising methylecgonidine or a derivative or analogue thereof having anticholinergic activity.

In above composition, the derivative or analogue is preferably selected from the group consisting of a compound of the formula:

wherein $R_2$ is H, $C_1$–$C_{10}$ alkyl or an amidine, and wherein $R_1$ is $C_1$–$C_{10}$ alkyl or an aryl substituted $C_1$–$C_{10}$ alkyl.

Most preferred MEG derivatives or analogues substituted at $R_1$ are selected from the group consisting of anhydroecgonine ethyl ester, anhydroecgonine propylester, anhydroecgonine-2β-carboxylic acid-2-(p-azidophenyl) ethylester, anhydroecgonine-2β-carboxylic acid-2-(p-isothiocyanatophenyl)ethylester, anhydroecgonine-2β-carboxylic acid-2-[p(bromacetoamido)phenyl]ethylester, anhydroecgonine-2β-carboxylic acid-2-(3-iodo-4-azidophenyl)ethylester, anhydroecgonine-2β-methyl ketone, anhydroecgonine-2β-ethyl ketone, anhydroecgonine-2β-isothiocyanate, and anhydroecgonine-2β-thiocyanate.

In a preferred embodiment of the above composition, $R_1$ is $CH_3$, and $R_2$ is a $C_1$–$C_{10}$ alkyl group or an amidine. Preferred derivatives or analogues substituted at $R_2$ are selected from the group consisting of N-methyl anhydroecgonine methylester, N-ethyl anhydroecgonine methylester, N-isopropyl anhydroecgonine methylester, N-propyl anhydroecgonine methylester, N-butyl anhydroecgonine methylester, N-sec-butyl anhydroecgonine methylester, N-tert-butyl anhydroecgonine methylester, N-guanidine anhydroecgonine methylester, N-formamidine anhydroecgonine methylester and N-acetamidine anhydroecgonine methylester.

The present invention also provides a method for preventing or inhibiting a muscarinic cholinergic response in a cell or tissue comprising providing to the cell or tissue an effective anticholinergic concentration of MEG or a derivative or analogue thereof having anticholinergic activity. In this method, preferred derivatives or analogues are those described in the compositions, above.

The present invention is also directed to a pharmaceutical composition useful for preventing or inhibiting bronchoconstriction in a subject comprising:

(a) MEG or a derivative or analogue thereof having anticholinergic activity, preferably a derivative or analogue as described above; and (b) a pharmaceutically acceptable carrier or excipient.

In another embodiment, the pharmaceutical composition further comprises:

(c) one or more medicaments useful for treating symptoms of pulmonary disease.

Preferred medicaments are selected from a group consisting of a β-adrenergic blocker, phosphodiesterase inhibitor, a mast cell stabilizing agent, an antihistamine and an anti-inflammatory agent.

The present invention also provides a method for preventing or treating bronchoconstriction in a subject, comprising administering to the subject an effective amount of a pharmaceutical composition, as above. The method is useful for treating bronchoconstriction associated with asthma, chronic obstructive pulmonary disease and pulmonary hypersensitivity.

The present invention is further directed to a compound having irreversible antimuscarinic anticholinergic activity, which compound is selected from the group consisting of a compound of the formula:

wherein $R_2$ is H, $C_1$–$C_{10}$ alkyl or an amidine, and wherein $R_1$ is a $C_1$–$C_{10}$ alkyl, to the omega carbon of which is bound a reactive organic moiety capable of binding covalently to a constituent of the surface of a cell after the compound has bound to a muscarinic receptor on the surface of the cell.

Preferred compounds having irreversible antimuscarinic activity are selected from the group consisting of anhydroecgonine-2β-carboxylic acid-2-(p-azidophenyl) ethylester, anhydroecgonine-2β-carboxylic acid-2-(p-isothiocyanatophenyl)ethylester, anhydroecgonine-2β-carboxylic acid-2-[p(bromacetoamido)phenyl]ethylester, anhydroecgonine-2β-carboxylic acid-2-(3-iodo-4-azidophenyl)ethylester, anhydroecgonine-2β-isothiocyanate and anhydroecgonine-2β-thiocyanate.

The present invention is further directed to a method of modifying an antimuscarinic compound to become an irreversible cholinergic inhibitor, comprising chemically adding to the compound a reactive organic moiety capable of binding covalently to a constituent of the surface of a cell after the compound has bound to a muscarinic receptor on the surface of the cell.

In another embodiment, the present invention provides a method for preventing or inhibiting a response to histamine in a cell or tissue comprising providing to the cell or tissue an effective antihistaminic concentration methylecgonidine or an antihistaminic derivative or analogue thereof.

BRIEF DESCRIPTION OF THE DRAWINGS

FIG. 1 shows a three-dimensional chemical structure of methylecgonidine (MEG). The shaded circles represent carbon atoms.

FIG. 2 shows the structure of cocaine and its pyrolysis product anhydroecgonine methyl ester (methylecgonidine or MEG). Also shown are the structures of the muscarinic antagonists arecoline and anatoxin, as well as the cholinergic compounds acetylcholine, nicotine and muscarine.

FIG. 3 is a graph showing that MEG non-competitively antagonized acetylcholine (ACh), reducing the tension produced by isolated tracheal rings in response to cumulative ACh concentrations (left). Acetylcholine alone (circle, Mean ±2 S. E., n=29) produced contraction at $10^{-8}$M and above. MEG reduced the magnitude of this contraction at all concentrations (inverted triangle, $10^{-9}$, n=6; triangle, $10^{-8}$, n=9; square, $10^{-7}$, n=6; diamond, $10^{-6}$, n=8), and was not surmountable by ACh. MEG at $10^{-9}$M and above reduced the peak tension produced by ACh ($2\times10^{-3}$M) (right). The fitted line (p=0.0106) is bounded by 95% confidence limits.

FIG. 4 is a graph showing that cocaine sensitized isolated tracheal rings to acetylcholine (ACh). ACh-induced tension (top, mean ±2 S. E., n=18,4,3,6,4,3) was increased by cocaine HCl concentrations ranging from $10^{-7}$ to $10^{-5}$M, and decreased at $10^{-4}$M. Cocaine increased the maximum tension produced ($2\times10^{-3}$M ACh; circles), throughout the range of ACh concentrations studied. Although cocaine did not produce tension in the absence of ACh, it did enable tension production at previously inactive ACh concentrations, e.g., $10^{-9}$M (triangle). The lowest concentration at which ACh produced a contractile response was reduced following a 5 min incubation with cocaine in the tissue bath (bottom).

FIG. 5 is a graph showing that MEG ($10^{-7}$M, square) non-competitively antagonized acetylcholine (circle). Cocaine ($5\times10^{-6}$M, triangle) lowered the threshold at which ACh produced tension by two orders of magnitude, and increased the maximum tension produced. MEG ($10^{-7}$M, diamond) non-competitively antagonized ACh in the presence of cocaine sensitization.

FIG. 6 is a graph showing that MEG at concentrations of $10^{-7}$ and $10^{-9}$M antagonized the contraction-inducing action of histamine on isolated tracheal rings.

DESCRIPTION OF THE PREFERRED EMBODIMENTS

Figure 1:
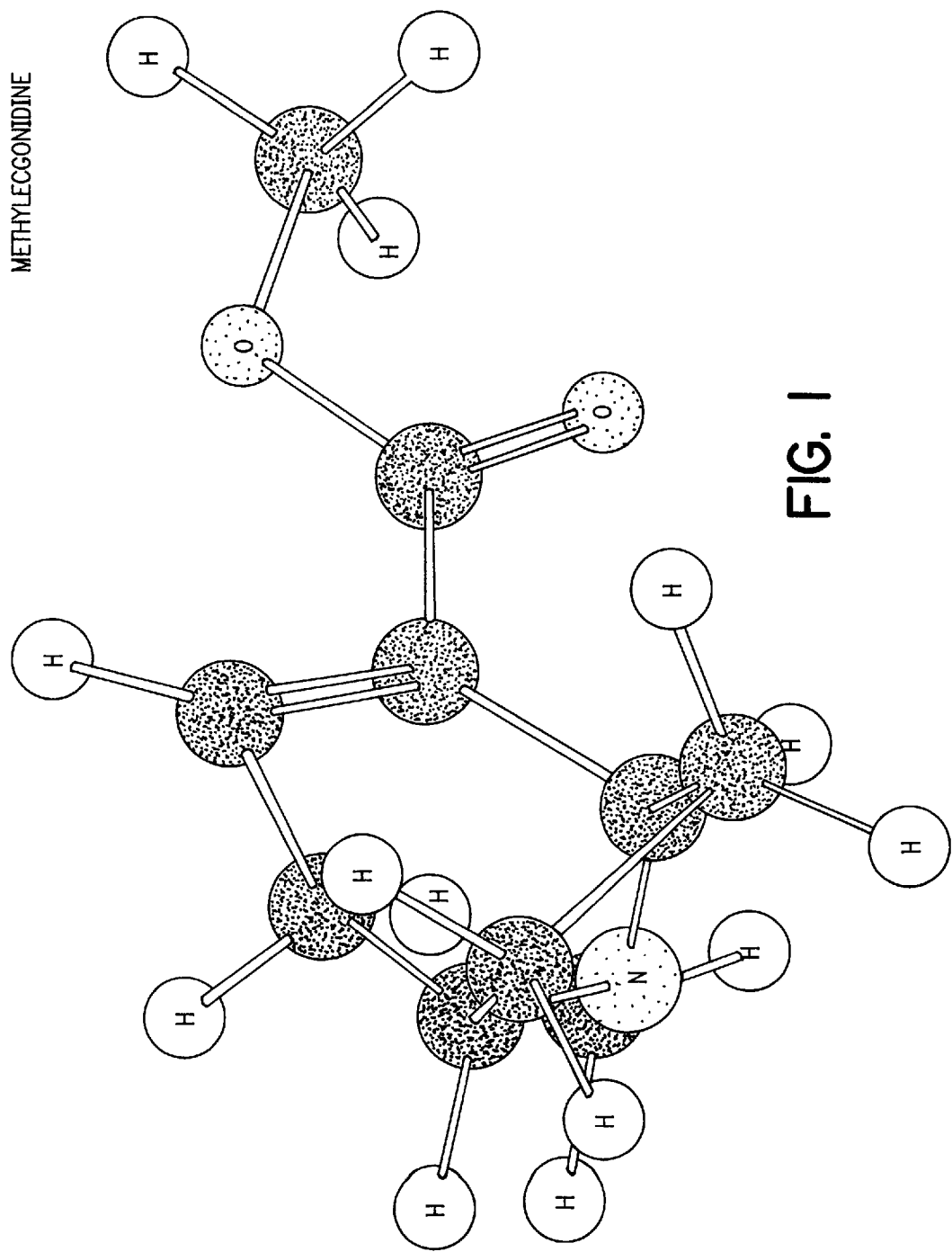

The present invention relates to novel cocaine derivatives, in particular MEG and anticholinergic analogues thereof, and to methods of using these compounds in the treatment of pulmonary diseases associated with bronchoconstriction and other diseases treatable by anti-cholinergic, antihistaminic and spasmolytic agents.

A. MEG AS AN ANTICHOLINERGIC AGENT

While investigating the effects of crack smoking, the present inventors noted that experimental animals frequently showed bronchoconstriction during inhalation of crack test atmospheres. This unexpected result led the present inventors to focus on methylecgonidine (MEG; anhydroecgonine methyl ester), a pyrolysis product formed during the heating of cocaine base (see FIGS. 1 and 2). MEG has been shown to act as a bronchoconstrictor when given alone by inhalation. It had been speculated that, because MEG resembled arecoline and anatoxin in structure (FIG. 2), this compound might be a cholinergic agonist.

The present inventors therefore performed a series of studies in isolated guinea pig tracheal rings (see Examples, below). Surprisingly, in light of the above speculation, MEG was found to lack any cholinergic agonist activity. Even more surprisingly, MEG turned out to be a potent non-competitive cholinergic antagonist in vitro. The antagonistic effects of MEG were insurmountable by the addition of increasing amounts of ACh. Furthermore the anticholinergic effects were irreversible; once the tracheal rings were exposed to MEG, the original magnitude of contraction could not be restored.

B. TREATMENT OF PULMONARY DISEASE AND OTHER DISEASES

The present invention provides compositions and methods for treating pulmonary diseases associated with bronchoconstriction including asthma, chronic obstructive pulmonary disease, pulmonary hypersensitivity, and the like.

In addition, the compositions and methods of the present invention are useful in the treatment of any disease or condition which is treatable with an anticholinergic agent, a spasmolytic agent or an anti-histaminic agent given orally, intranasally or by injection.

One example is the use of an anticholinergic compositions of the present invention to treat nasal symptoms of the common cold by administration as a nasal spray. It would have an advantage over current drugs (oxymetazoline, etc.) in that a single or very few administrations would be expected to suffice for the duration of the cold.

In addition, the compositions and methods of the present invention are useful in the treatment of pulmonary and gastrointestinal (GI) symptoms of cystic fibrosis. After opening the airways, for example with a β2-adrenergic agonist, MEG or an analogue thereof, preferably N-isopropylMEG, is administered to the airway to inhibit mucus secretion. In addition, MEG or its analogue is given orally to inhibit mucus secretion in the GI tract. The compounds of the present invention have the advantage that their systemic absorption in the GI tract is minimal, while they can act on the mucus producing cells of the gut wall.

Similarly, oral administration of the compositions of the present invention can be used to treat GI ulcers by inhibiting ulcerogenic secretion in the stomach or duodenum. Alternatively, the compositions of the present invention are useful to inhibit undesired gastric motility associated with a number of diseases (Gilman et al., supra).

Different classes of drugs used to treat various symptoms of diseases, in particular bronchopulmonary diseases, have been discussed above.

Compositions of the present invention with anticholinergic activity, preferably MEG, are particularly useful in treating the above-mentioned pulmonary diseases.

The preferred animal subject of the present invention is a mammal. The invention is particularly useful in the treatment of human subjects.

By the term "treating" is intended the administering to subjects of MEG, or a chemical derivative or analogue thereof having anticholinergic activity, for purposes which may include prevention, amelioration, or cure of pulmonary diseases associated with bronchoconstriction. Also intended within the scope of the present invention is the treatment of any disease treatable by anticholinergic, spasmolytic or antihistaminic agents.

A pharmaceutical composition of the present invention comprises MEG, or an anticholinergic derivative thereof and a pharmaceutically acceptable carrier or excipient.

In another embodiment, the pharmaceutical composition may comprise MEG or its derivative, in combination with another medicament useful in treating one or more symptoms of the disease, for example a β-adrenergic agonist or an anti-inflammatory steroid. Medicaments are considered to be provided "in combination" with one another if they are provided to the patient concurrently or if the time between the administration of each medicament is such as to permit an overlap of biological activity.

The pharmaceutical composition of the present invention may be administered by any means that achieves its intended purpose. Amounts and regimens for the administration of MEG or its derivative can be determined readily by those with ordinary skill in the clinical art of treating pulmonary disease.

For example, administration may be by parenteral, subcutaneous, intravenous, intramuscular, intraperitoneal, transdermal, or buccal routes. Alternatively, or concurrently, administration may be by the oral route. Preferred routes are by nasal or oral inhalation, intranasal administration by spray, and oral (enteral) administration. The route and the dosage administered will be dependent upon the age, health, and weight of the recipient, kind of concurrent treatment, if any, frequency of treatment, and the nature of the effect desired.

Compositions within the scope of this invention include all compositions wherein the MEG or derivative or analogue thereof is contained in an amount effective to achieve its intended purpose. While individual needs vary, determination of optimal ranges of effective amounts of each component is within the skill of the art. Typical dosages of MEG, or a derivative thereof, comprise 1 ng/kg/body wt. to 100 mg/kg/body wt. The preferred dosages comprise 0.001 to 10 mg/kg/body wt. The most preferred dosages comprise 0.01 to 1 mg/kg/body wt.

In addition to the pharmacologically active compound or compounds, the pharmaceutical composition preferably contains one or more suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20% to 75% of active compound(s), together with the excipient.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers may be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

A pharmaceutical composition for systemic administration according to the invention may be formulated for enteral, parenteral or topical administration. Indeed, all three types of formulation may be used simultaneously to achieve systemic administration of the active ingredient.

Suitable formulations for oral administration include hard or soft gelatin capsules, dragees, pills tablets, including coated tablets, elixirs, suspensions, syrups or inhalations and controlled release forms thereof. Solid dosage forms in addition to those formulated for oral administration include rectal suppositories. MEG or its derivative may also be administered in the form of an implant.

Suitable formulations for topical administration include creams, gels, jellies, mucilages, pastes and ointments. The compounds may also be formulated for transdermal administration, for example, in the form of transdermal patches so as to achieve systemic administration.

Suitable injectable solutions include intravenous subcutaneous and intramuscular injectable solutions. The MEG or derivative may also be administered in the form of an infusion solution or as a nasal inhalation or spray.

C. MECHANISMS OF MEG ACTION

Several mechanisms may account for the irreversibility of the anticholinergic properties of MEG observed by the present inventors (see Examples, below), although the inventors do not wish to be bound by any particular mechanism or mechanisms of action.

Cocaine is a bicyclic alkaloid with two ester functional groups: a benzoate ester, and a carboxyl methyl ester. Debenzoylation occurs in the presence of plasma cholinesterase. Benzoyl choline is also a substrate for this enzyme, and has a strong structural resemblance to half the tropane ring of cocaine. The methyl ester functional group undergoes spontaneous hydrolysis at physiological pH, leaving a carboxylic acid group (T. Inaba, *Can. J. Physiol. Pharmacol.* 67:1154–1157 (1989).

It is postulated that the irreversibility of the biological effect results from the formation of a ligand-receptor complex of MEG and the muscarinic receptor, followed by the formation of a covalent hydrogen bond between the carboxylic acid moiety with a site on the adjacent membrane surface.

Despite the observed irreversibility, the existence of receptor turnover would be expected to result in a limited duration of the effect. Although one would expect prompt relief, an agent with prolonged effects has particular utility for prophylactic use where administration may be less frequent. Thus it would be expected that MEG or a similarly acting derivative would have an advantage over other drugs. For example, it would be less likely to induce overuse like β-adrenergic agonists with their attendant risks of tolerance and toxicity. Furthermore, a long-acting anticholinergic agent such as MEG or another anticholinergic compound rendered "irreversible" as described below, which is presently not available, would be particularly suitable for the treatment of nocturnal asthma.

It is expected that MEG or a derivative thereof will have a broader spectrum of pharmaceutical effects than ipratropium. For example, MEG has antihistaminic activity as well as anticholinergic activity. Thus, it could contribute to the treatment of bronchoconstriction by this additional mode of action (Page, supra). A single agent with multiple desirable activities would be preferable to a drug having a limited activity via a single receptor system, such as ipratropium.

The results presented in the Examples below indicate that MEG does not shift the threshold for an ACh-induced contraction, but rather reduces the magnitude of the response to the agonist. Therefore, in a patient treated with MEG, a noncompetitive cholinergic antagonist, the symptoms warning of incipient bronchoconstriction, such as those caused by exposure to a low level of allergen may be unaffected. Importantly, the protective function of bronchoconstriction could still occur but at reduced amplitude. In contrast to the action of MEG, a competitive antagonist might obliterate warning properties and inhibit the desirable airway responses which result in a minimization of exposure. In that setting, bronchoconstriction might not result until a large provocation has occurred, increasing the risk of maximal bronchoconstriction and death. Use of a non-competitive antagonist such as MEG or its derivatives would block the maximum possible tissue response, resulting in a saving of lives.

Under circumstances of extreme hyperresponsiveness, such as in a severe case of asthma, however, it may be preferably to completely obliterate pulmonary responsiveness. For such a situation, chronic over-administration of MEG could be employed to achieve a functional ablation of the muscarinic receptor population within the lung.

D. CHEMICAL MODIFICATION OF MEG AND ITS ACTIVE DERIVATIVES

Figure 2:
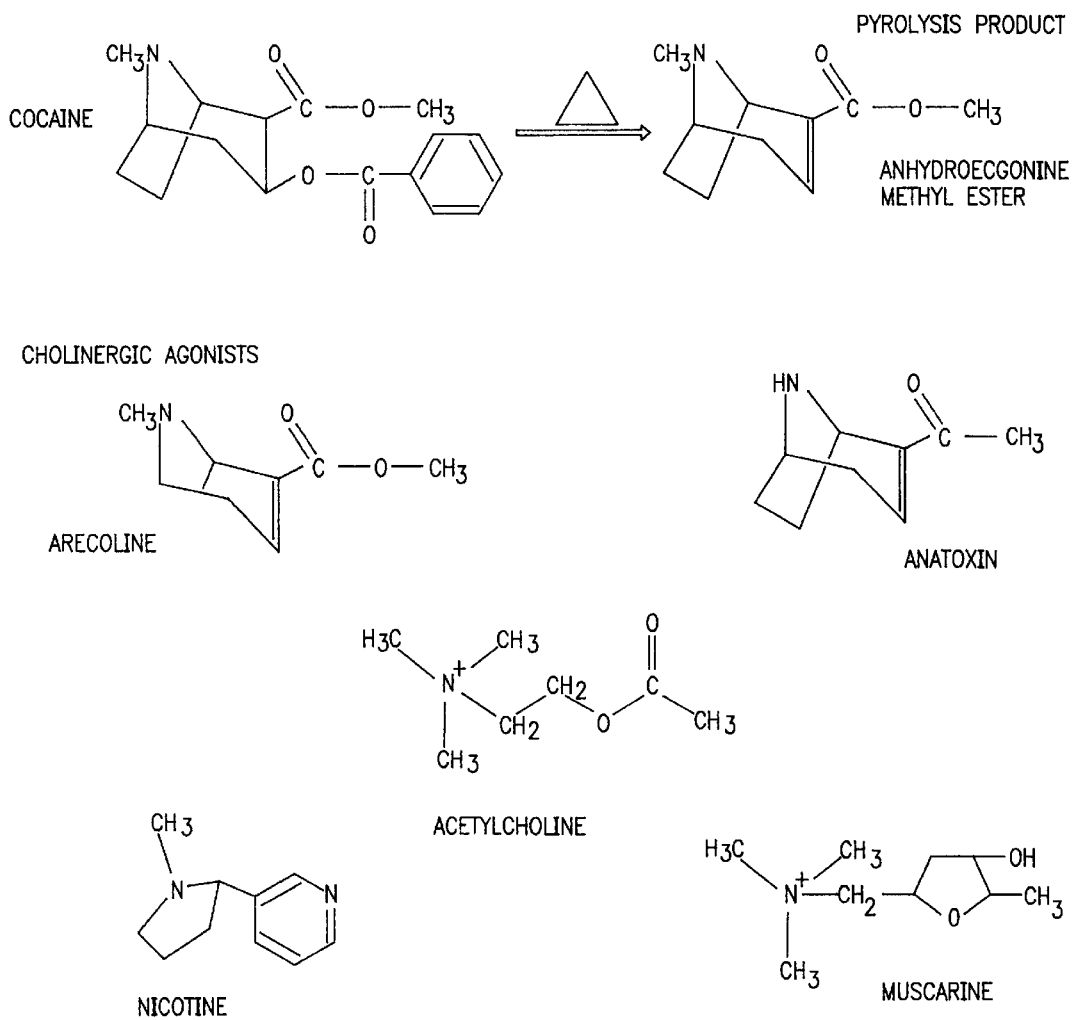
Figure 3A:
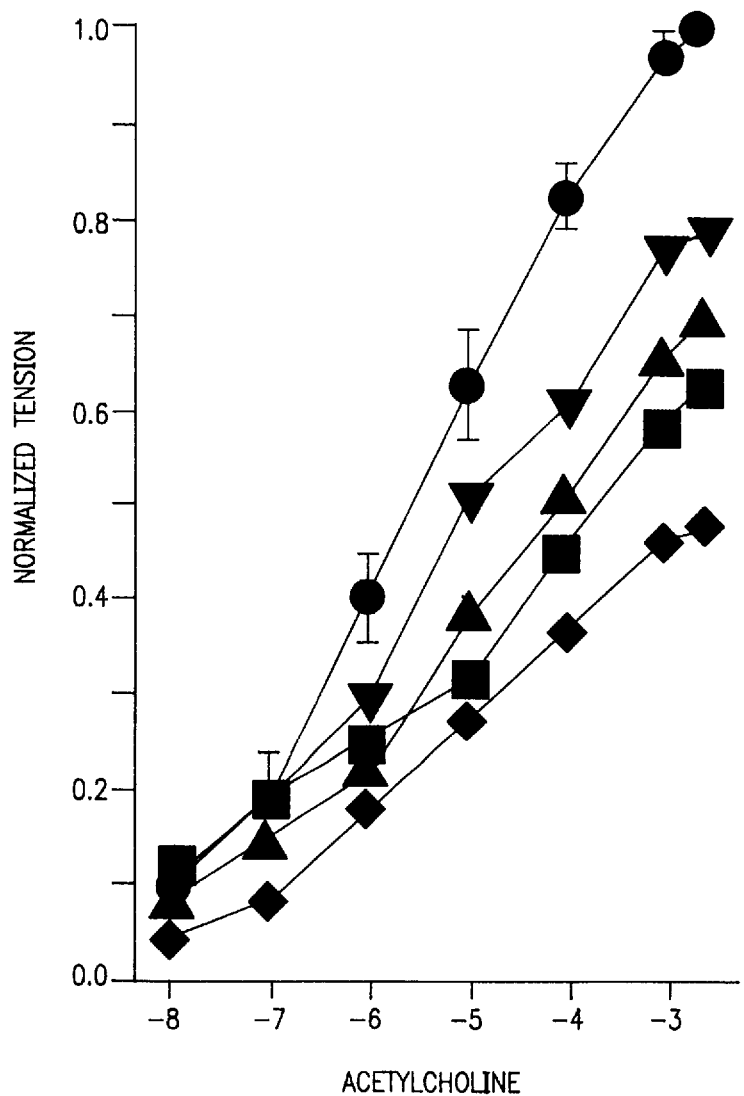
Figure 3B:
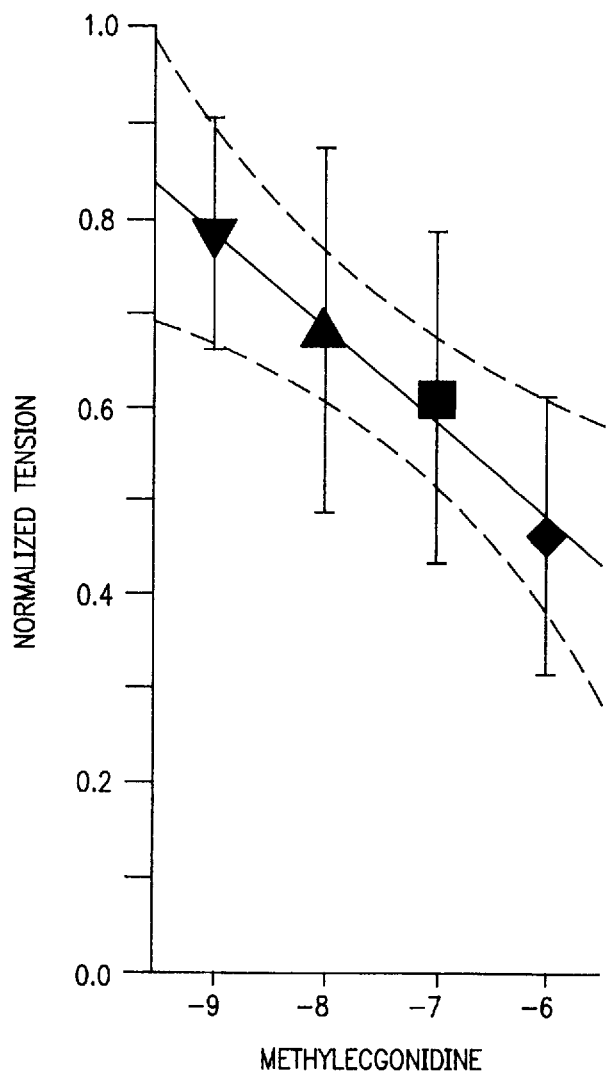

The structure of MEG is as follows (see also FIGS. 1 and 2).

A number of other modifications of the tropane ring at any of two sites ($R_1$ or $R_2$; see below) in the molecule are included within the scope of the present invention. The structures described herein can be substituted in any one of three sites as indicated.

"Alkyl" means a branched or unbranched, saturated hydrocarbon chain containing 1–10 carbon atoms, such as methyl, ethyl, propyl, tert-butyl, n-hexyl and the like. "Optionally aryl substituted alkyl" means a moiety in which a substituted or unsubstituted phenyl or other aryl group (including a heterocyclic ring) may or may not be attached to the omega carbon of the alkyl group, as defined herein.

Below is a list of preferred substituents at the two indicated positions in the structure:

The names of the compounds provided for the $R_1$-substituted compounds are based on the single noted substitution, where $R_2$ is a hydrogen atom. Preferred $R_1$ include $C_{1-10}$ alkyl groups, which may be optionally aryl substituted. Preferably, the alkyl group or aryl substituted alkyl group is an active alkylating moiety or a group reactive with a cell surface component capable of forming a covalent bond. Preferred substitutions at $R_1$ are:

(1) $CH_3$ (anhydroecgonine methylester or MEG);
(2) $CH_2CH_3$ (anhydroecgonine ethyl ester);
(3) $(CH_2)_2CH_3$ (anhydroecgonine propylester);
(4) $(CH_2)_2C_6H_4$ 4-$N_3$ (anhydroecgonine-2β-carboxylic acid-2-(p-azidophenyl)ethylester;
(5) $(CH_2)_2C_6H_4$ 4-NCS (anhydroecgonine-2β-carboxylic acid-2-(p-isothiocyanatophenyl)ethylester;
(6) $(CH_2)_2C_6H_4$ 4-$NHCOCH_2Br$ (anhydroecgonine-2β-carboxylic acid-2-[p(bromacetoamido)phenyl]ethylester;
(7) $(CH_2)_2C_6H_{3\text{-}I}$ 4-$N_3$ (anhydroecgonine-2β-carboxylic acid-2-(3-iodo-4-azidophenyl)ethylester;
(8)

In the following four embodiments, the $COOR_1$ group is replaced with: $COCH_3$ (anhydroecgonine-2β-methyl ketone);
(9) $COCH_2CH_3$ (anhydroecgonine-2β-ethyl ketone);
(10) NCS (anhydroecgonine-2β-isothiocyanate); and
(11) SCN (anhydroecgonine-2β-thiocyanate).

$R_1$ substituents (1) to (3) above are MEG or alkylester variants of MEG. Substituents (4)–(7) are modelled on potential irreversible ligands for the dopamine transporter described by Carroll et al., *J. Med. Chem.* 35:1813–1817 (1992). Substituents (8) and (9) are 2β-alkylketone variants of MEG (*Eur. J. Pharinacol.* 244:93–97 (1993)). Substituents (10) and (11) are mustards.

Preferred cocaine derivatives are MEG analogues in which the carboxymethyl ester moiety of MEG is replaced by a substituent group which is an alkylating moiety or other reactive group which will form a covalent bond with the muscarinic receptor after ligand-receptor interaction. Preferred reactive groups are electron-withdrawing groups, including halide substituted aryl groups, and the like. By covalently bonding to the cell surface, presumably to the muscarinic (or other) receptor, such a derivative will have a relatively irreversible anticholinergic mode of action. Of the compounds listed above, substituents (4)–(7), (10) and (11) have such properties (Carroll et al., supra)

β-funaltrexamine (β-FNA), the fumaramate methyl ester of naltrexamine is a narcotic antagonist having an alkylating moiety through which the compound binds irreversibly to the membrane after the ligand-receptor interaction. This agent does not provoke up-regulation of the number of receptors, as occurs with other narcotic antagonists. On the basis of these properties, a fumamarate methyl ester analogue of MEG is a useful anticholinergic agent in accordance with the present invention. Another example is acetylethylcholine mustard, which is a cholinergic agonist that irreversibly binds to the muscarinic receptor.

Preferred substituents at the $R_2$ position (where the names are directed to compounds in which $R_1$ is methyl) include:
(1) H (anhydroecgonine methylester, MEG);
(2) $CH_3$ (N-methyl anhydroecgonine methylester);
(3) $CH_2CH_3$ (N-ethyl anhydroecgonine methylester);
(4) $CH(CH_3)_2$ (N-isopropyl anhydroecgonine methylester);
(5) $CH_2CH_2CH_3$ (N-propyl anhydroecgonine methylester);
(6) $CH_2CH_2CH_2CH_3$ (N-butyl anhydroecgonine methylester);
(7) $CH_3(CH)CH_2CH_3$ (N-sec-butyl anhydroecgonine methylester);
(8) $C(CH_3)_3$ (N-tert-butyl anhydroecgonine methylester); and
(9) an amidine such as guanidine, formamidine or acetamidine.

Alkyl substituents at the bridge nitrogen result in the formation of quaternary compounds with limited solubility in lipid and reduced access to the central nervous system. Absorption from the lung into the bloodstream is not expected for the isopropyl or larger compounds. By varying the substituents, one or ordinary skill in the art may alter the pharmacokinetic profile and produce more selective effects between organs when the compound is administered systemically. Replacing the "cationic head" of MEG and derivatives thereof with an amidine basic center may be useful for altering both the pharmacokinetics and pharmacodynamics of the compound (Cereda et al., *J. Med. Chem.* 33:2108–2113 (1990)). This may influence relative potency and selectivity at muscarinic or histamine receptors, which is of particular interest when the compound is administered systemically.

The stereochemistry of the $R_2$ substituents is expected to alter the pharmacologic potency of the compound. When oriented over the pyrrolidine ring, lesser potency is expected than when the substituent is oriented over the piperidine ring., i.e., endo to the three atom bridge of the tricyclic tropinol skeleton. Synthesis of the compound having the endo configuration can be performed according to Deckers, W., *Postgrad. Med. J.* 51(Suppl. 7):76–81 (1975). For example, a Robinson-Schopf condensation of succindialdehyde, isopropylamine and acetonedicarboxylic acid produces isopropylnortropinone which can be hydrogenated catalytically to isopropylnortropine.

A most preferred MEG analogue modification involves substituting at the nitrogen in the $R_2$ position an isopropyl group resulting in a quaternary amine which would enhance the organ selectivity of MEG to the lung on the basis of pharmacokinetic properties.

An additional substitution involves replacement of the C—C bond between $C_6$ and $C_7$ in the tropane ring (the pyrrolidine ring portion) with an epoxide structure, thereby introducing an additional 3-membered ring having an oxygen atom at one "vertex". Scopolamine, a well-known anticholinergic compound, is such an epoxide of atropine.

On the basis of the observed action of MEG in light of its structure, the present invention is also directed to other irreversible anticholinergic agents based on chemical modification of atropine. For example, atropine is modified by adding a fumaramate methyl ester or mustard or carboxyl methyl ester moiety, or other reactive groups, such as those described above as $R_1$ substituents, which will covalently bind to the muscarinic receptor upon ligand-receptor interaction. Such an atropine derivative would serve as an "irreversible atropine." For example, esterification of atropine with α-formylphenacetic acid results in the formation of an ester which is reduced to isopropylnoratropine, which can then be quaternized with methylbromide (Deckers, supra).

It is currently believed by the present inventors that the irreversible effects of MEG are attributable to the interaction between this molecule and a receptor to which it binds. This may take the form of a Michael reaction in which the double bond opens and a new bond forms in its proximity. If this is the case, any of a number of electron-withdrawing substituents can be located in the $R_1$ position (see above), as long as the α-β unsaturated nature of the parent compound remains undisturbed. If the irreversibility is a property of the $R_1$ moiety itself rather than its effect of withdrawing an electron from the piperidine ring, then more reactive substituents in that position on MEG or on atropine would be preferred.

Having now generally described the invention, the same will be more readily understood through reference to the following examples which are provided by way of illustration, and are not intended to be limiting of the present invention, unless specified.

EXAMPLE I

MEG HAS ANTICHOLINERGIC ACTIVITY IN VITRO

A. MATERIALS AND METHODS

1. Preparation of Tracheal Rings and Measurement of Contraction

After injection of a lethal dose of sodium pentobarbital and loss of reflex to painful stimulation, a section of guinea pig trachea was removed, trimmed of excess connective tissue, and tracheal rings prepared from the distal region proximal to the bifurcation (P. M. Vanhoutte. *Am. Rev. Respir. Dis.* 6:S24 (1988)).

Each ring was mounted in a 10 ml organ bath containing Krebs-Henseleit solution at 37° C. and aerated with a mixture of 95% $O_2$ and 5% $CO_2$. Tissues were allowed to equilibrate for 1 hr, under resting tensions of 1.25 g. The bathing fluid was changed at intervals of 10–15 min. Tension generated by tissue contraction was measured with isometric transducers connected to a polygraph (Transducer Model FT03 connected to a Grass Model 7 polygraph; Grass Medical Instruments Co., Quincy, Mass.).

2. Responses to Acetyl Choline (ACh) and Testing of Cocaine Derivatives

Cumulative ACh concentration-response curves were established (J. M. Van Rossum. *Arch. Int. Pharmacodyn.* 143:219 (1963)) at concentrations ranging from $10–^{10}$ to $2\times10^{-3}$M by adding successive aliquots of 0.1 ml. After the highest ACh concentration came to plateau, the bath was repeatedly drained and replenished, allowing the tissue to relax.

Methylecgonidine fumarate or cocaine hydrochloride (Research Triangle Institute, Research Triangle Park, N.C.) were then introduced into the bath and the tissue incubated for 5 minutes. Cumulative dose-response curves to ACh were again established in the presence of single concentrations of MEG and/or cocaine. Tissue responses were expressed as the proportion of the maximum response the same ring exhibited during the preceding ACh treatment series.

B. RESULTS AND DISCUSSION

Once tracheal rings had been exposed to MEG, full responsiveness to ACh could not be restored. In contrast, full responsiveness to ACh after cocaine (at concentrations below $10^{-4}$M) was restored with no desensitization.

MEG reduced the magnitude of contraction produced by ACh without changing the tissue threshold of contraction (FIG. 3, left). The effects of MEG could not be overcome even by increasing the ACh concentration to concentrations as high as $2\times10^{-3}$M.

The magnitude of maximum tension reduction was concentration-related (FIG. 3, right). In other experiments, MEG at $10^{-7}$M (the concentration that reduced the maximum amplitude of the response to ACh by half), was comparably effective in non-competitively reducing contractions induced by carbachol.

Others have demonstrated that $10^{-7}$M atropine shifted the carbachol cumulative concentration response function to the right, and this effect was surmountable at $10^{-4}$M carbachol (J. M. Drazen et al., *J. Clin. Invest.* 61:1441, (1978)). The present inventors, using carbachol as the agonist, found an insurmountable 50% reduction at equimolar concentrations of MEG. The magnitude of reduction observed at any given concentration of carbachol in the presence of $10^{-7}$ atropine was usually less than that produced by MEG. H. S. Orer et al., *Arch. Int. Pharmacodyn.* 305:45 (1990) demonstrated that atropine at 3, 10 and 30 nM competitively antagonized ACh-induced contraction of guinea pig tracheal rings with recovery of maximal contractile response after removal of the antagonist. In contrast, MEG produced an insurmountable non-competitive antagonism at 1 nM and above, with no recovery after washing of the preparation. Thus, compared with the effects of atropine on cholinergic agonist-induced contraction of guinea pig tracheal smooth muscle, MEG is more effective in reducing the magnitude of response and is irreversible under the conditions examined.

As observed by the present inventors, MEG was ineffective in altering the amplitude of tension produced by supra-maximal electrical stimulation, or ACh-produced contraction of the chicken biventer cervicis muscle in vitro, an assay for antinicotinic activity (B. L. Ginsborg et al., *Br. J. Pharmacol.* 15:410 (1960); H. A. N. El-Fawal et al., *Neurotoxicology* 9:625 (1988)).

The addition of MEG to the bath following pre-contraction of tracheal rings with $10^{-3}$ ACh, produced a dose-dependent relaxation of the tracheal preparation, but this occurred at concentrations two orders of magnitude higher than those shown to antagonize ACh-induced contraction when the tissue is preincubated with MEG. However, this relaxation was not due to any agonistic activity since MEG failed to relax tracheal rings with mechanically elevated tension. Thus both the presence of ACh and its displacement from the receptor site by MEG apparently are necessary to produce relaxation, suggesting that MEG has affinity for the muscarinic ACh receptor.

Figure 4A:
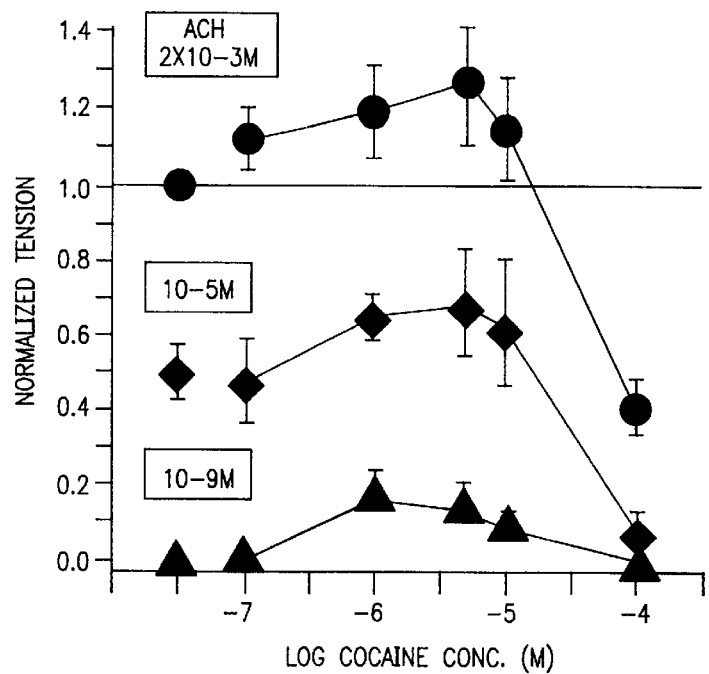
Figure 4B:
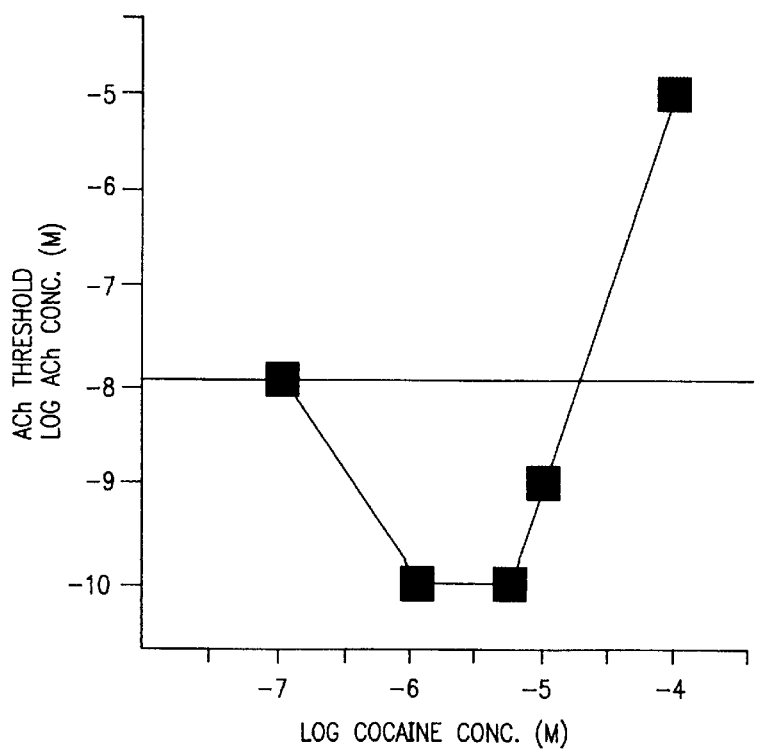

Cocaine did not display any spasmogenic activity by itself; however, cocaine at $10^{-6}$M lowered the threshold for contraction elicited by ACh (FIG. 4, bottom). Furthermore, cocaine at $10^{-7}$M increased the tension produced by ACh at the highest ACh concentration, $2\times10^{-3}$M (FIG. 4, top). This sensitization was dose-related, and occurred across ACh concentrations. At $10^{-4}$M, cocaine increased the threshold, and reduced the maximum response to a third of that produced by ACh alone. Such shifts in threshold have been seen before in isolated guinea pig atria at comparable concentrations (J. Sharkey et al., *J. Pharmacol. Exp. Ther.* 246:1048 (1988)), as well as in other preparations (K. L. Swanson et al., *J. Pharmacol. Exp. Ther.* 243:1202 (1987)). These effects may be related to cocaine's apparent local anesthetic properties at this concentration. However, cocaine from $10^{-4}$M to $2\times10^{-3}$M, when added to tissue pre-contracted with ACh, resulted in a further increase in dose-dependent tension. Cocaine might produce sensitization to ACh and potentiate its efficacy by preferentially occupying "silent" ACh receptors (A. Goldstein, *Pharmacol. Rev.* 1:102 (1949), cited in E. J. Ariens, *Molecular Pharmacology*, Academic Press, New York, vol. 1, 1964, pp. 107–109) when tissue is preincubated with cocaine, or by displacing ACh from "silent" receptors when given after pre-contraction with ACh, thus ACh would be made available to interact with functional receptors.

Figure 5:
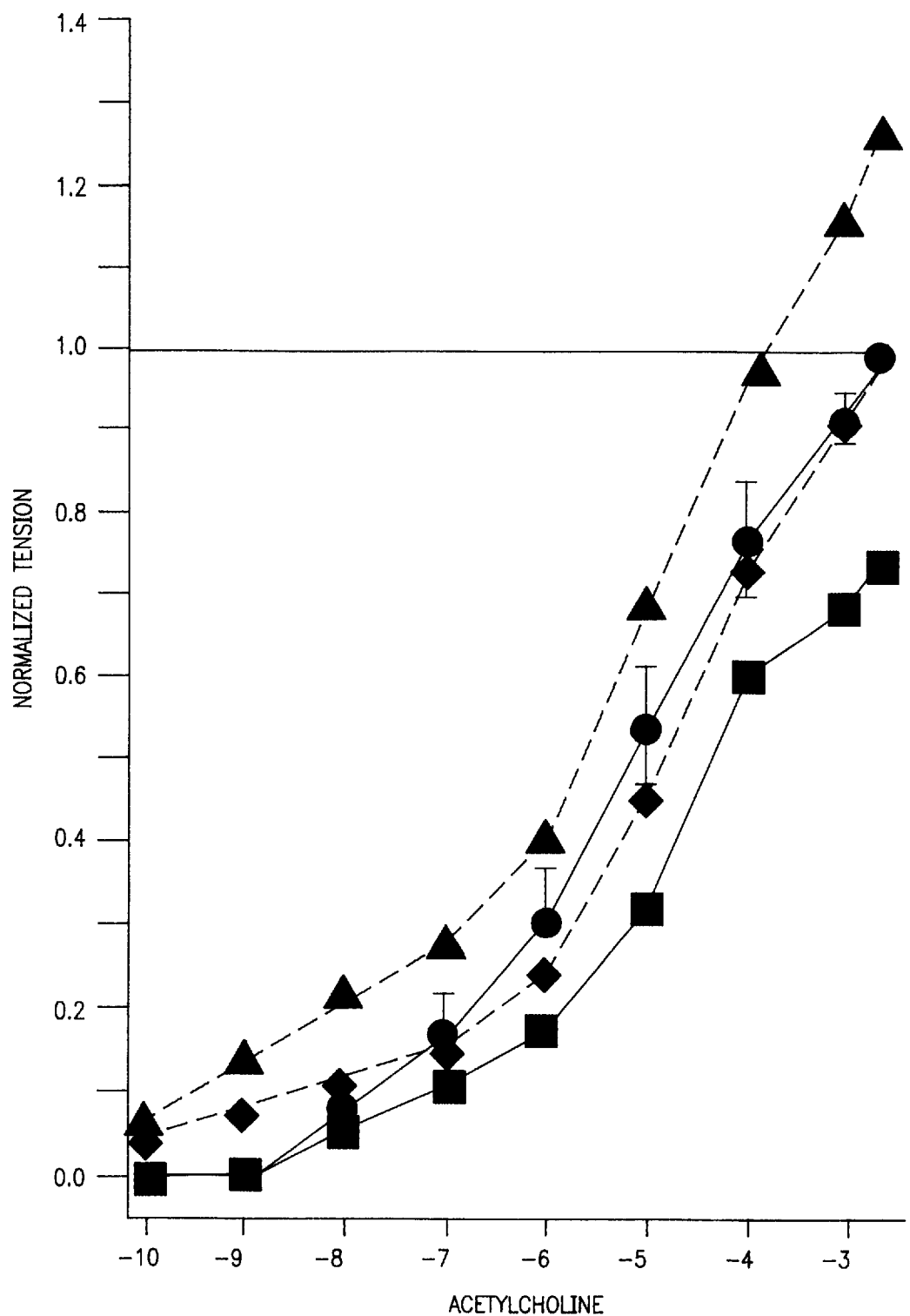

MEG antagonized cocaine's potentiation of acetylcholine's efficacy. It did so without modifying cocaine's ability to sensitize the tissue to ACh by two orders of magnitude (FIG. 5). Cocaine itself has antimuscarinic properties at $1.8\times10^{-5}$M as assayed by QNB binding (Sharkey et al., supra), a level from 4 to 20 times higher than that associated with euphoric states (R. W. Foltin et al. *Drug Alcohol Depend.* 26:145 (1990); M. W. Fischman et al., *Pharmacol. Biochem. Behav.* 18:123 (1983)).

Figure 6:
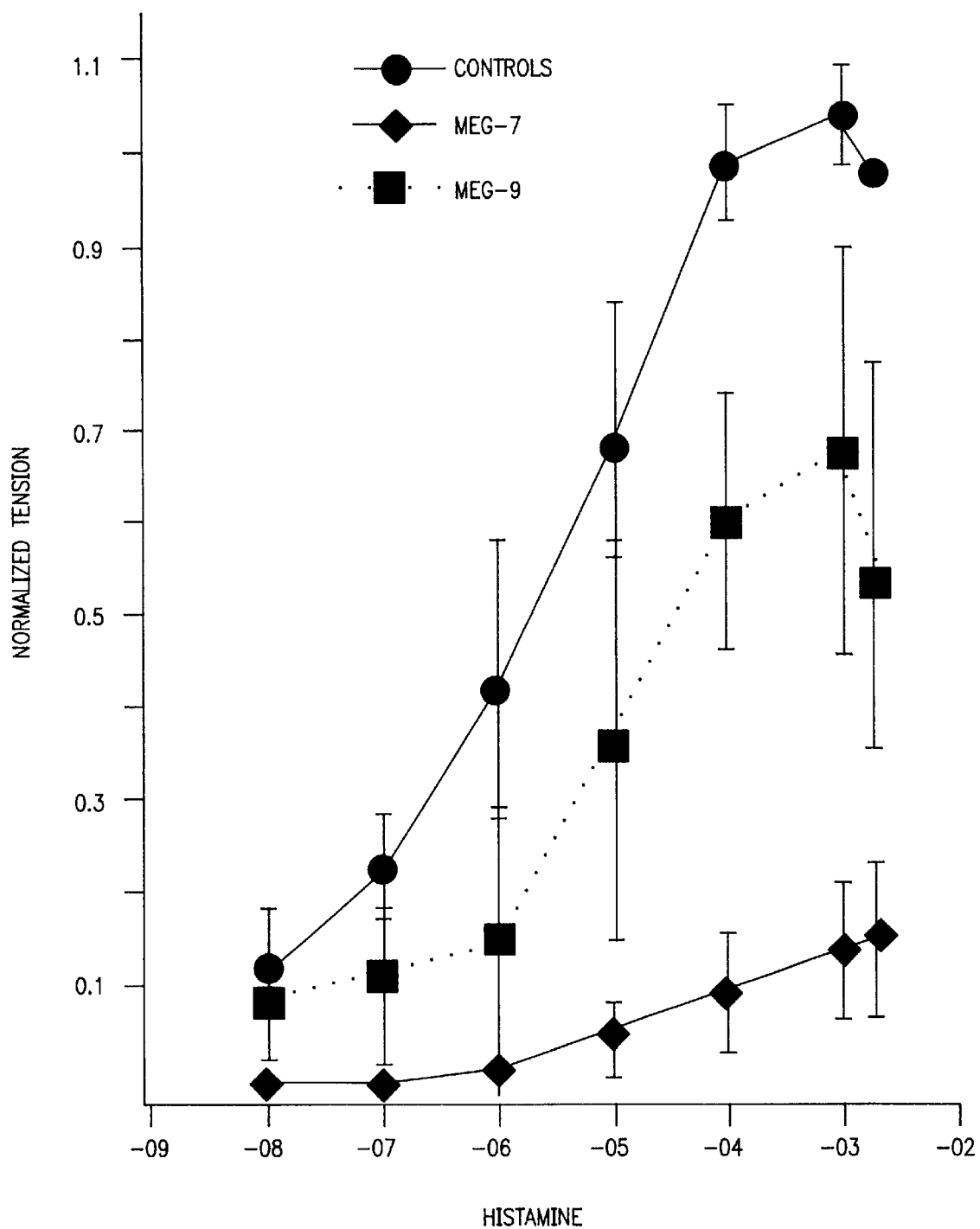

MEG displayed evidence of antihistaminic activity (see FIG. 6), insurmountably reducing the maximum amplitude of the histamine response at $2\times10^{-3}$ following a 5 min incubation at $10^{-9}$, and shifting the histamine threshold upwards at $10^{-7}$. This was studied in the same tracheal ring preparation described above.

The present study demonstrated anticholinergic properties of the major pyrolysis product of cocaine, MEG, at levels as low as $10^{-9}$M, a much lower concentration than that at which cocaine itself exerts such activity. MEG at $10^{-7}$M reduced the sensitization to ACh produced by cocaine at $5\times10^{-6}$M, a 1:50 ratio of MEG to cocaine reasonably expected to occur during crack smoking.

The findings reported here raise new concerns about the adverse consequences of crack smoking. Cocaine produced sensitization of tracheal rings to the effects of ACh, thus cocaine may lower the threshold for bronchoconstrictive episodes in crack smokers, as well as increase the severity of the asthmatic attack, regardless of the provoking event. This also would be consistent with clinical anecdotes of adverse effects of cocaine in asthmatics (Rubin et al., supra; Rao et al., supra).

The anticholinergic activity of MEG is incompatible with its being a cholinergic agonist as others have speculated (Jacob III et al., supra).

Based on the results presented above, it is still not clear how exposure to cocaine and its pyrolysis products provokes bronchoconstriction in and of itself. Irritation from the alkaline particles may play a role. The concentrations of MEG which show anticholinergic effects, as described above, indicate that MEG may have the capacity to exaggerate the cardiotoxicity of cocaine. Since anticholinergic drugs can prevent vagal inhibition of heart rate, MEG might aggravate the heart rate acceleration produced by cocaine itself.

If the actions of MEG resemble atropine, a prototypical antimuscarinic (anticholinergic) drug, MEG alone would probably have low abuse potential (D. M. Penetar et al., *Pharmacol. Biochem. Behav.* 24:1111 (1986)), but also might produce behavioral disruption (S. T. Higgins et al., *Pharmacol. Biochem. Behav.* 34:303 (1989)) that can be potentiated by central stimulants (M. C. Wilson et al., *Pharmacol. Biochem. Behav.* 3:363, 1975)). Thus MEG could aggravate clinically significant behavioral toxicities.

Furthermore, atropine increases the frequency of amphetamine (W. M. Davis et al., *Life Sci.* 16:237 (1975)) or cocaine self-administration (Wilson et al., *Pharmacol. Biochem. Behav.* 1:643, 1973)), as if by reducing the unit dose of stimulant delivered. Alternatively, this rate increase might result from reducing a process that interferes with self-administration, either an incompatible behavior or an aversive event (Wilson, 1975, supra). If MEG exerts similar actions, an individual smoking crack might be co-administering an agent that increases the frequency of cocaine use, or, worse, cocaine's reinforcing efficacy.

These potential adverse effects of cocaine pyrolysis products warrant determining if the effects observed at nanomolar concentrations with tracheal rings in vitro are predictive of effects seen in other tissues, and in the whole organism. Such studies were done and are reported in Section 7, below. If alterations in cholinergic function produced by cocaine pyrolysis products prove to play an important role in modifying the actions of cocaine base, a new strategy for developing pharmacologic treatments for cocaine abuse might emerge.

EXAMPLE II

ADMINISTRATION OF MEG IN VIVO

The present inventors undertook a series of experiments in laboratory primates examining the effects of MEG administered by the intravenous and inhalation routes of exposure.

Squirrel monkeys or guinea pigs were restrained in a whole body plethysmograph, a sealed box with a separate face mask for each animal. A pneumotachograph and stain gauge assembly permitted the measurement of flow. The ratio of derivatives of flow to box pressure yield a measure of airway conductance (SGAW). MEG was administered at concentrations up to 15 mg/liter of air. Bronchoconstriction was observed, presumably attributable to either particle loading of the lung or to the alkaline challenge (the test atmosphere is a base administered in the absence of water).

Based on the in vitro data, it was expected that cocaine would facilitate bronchoconstriction following exposure of the animals to acetylcholine or methacholine. It was further expected that MEG would antagonize these changes.

This was studied by exposing a population of squirrel monkeys, which were well-trained and adapted to the experimental setting, to aerosolized cholinergic agonists and then studying the effects of MEG or cocaine pretreatment on the response to cholinergic provocation.

To their great surprise, the present inventors were unable to produce bronchoconstriction in response to these standard agents. While these animals had no previous exposure to ACh or methacholine, they had extensive histories of exposure to MEG.

Care was taken to exclude any other source of potential measurement artifact, including reducing dead volumes, examining for leaks, recalibration, and so forth. The particles were dehydrated to reduce their size and facilitate airway entry. The monkeys' nares were occluded to compel mouth breathing. Greater methacholine concentrations in the nebulizer were tested in which dramatic decreases in heart rate occurred, consistent with significant systemic absorption of this relatively short duration cholinergic agonist. Despite evidence of prompt systemic cholinergic responses, there was no bronchoconstriction observed in these studies.

These observations were consistent with the in vitro findings described above. In fact, the in vivo effects were more sustained and dramatic than anticipated based on the in vitro results.

To verify that the measurement system was capable of measuring bronchoconstriction in these animals, histamine was administered by inhalation, producing bronchoconstriction, but only at unusually high levels. This may reflect the antihistaminic activity of MEG observed in vitro. This result demonstrates that the lack of bronchoconstriction in animals pretreated with MEG was not a measurement artifact.

It is noteworthy that MEG had a wide margin of safety in these studies. Only one exposed guinea pig died, after exposure to an extremely high concentration of MEG (14 mg/liter of air) given by inhalation. Guinea pigs are known to be highly sensitive to pulmonary manipulations.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A compound having the chemical formula:

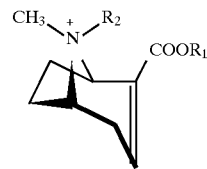

wherein $R_2$ is H, $C_1$–$C_{10}$ alkyl or an amidine; and wherein $R_1$ is $C_1$–$C_{10}$ alkyl, to the omega carbon of which is bound a reactive organic group capable of binding covalently to a constituent of the surface of a cell after said compound has bound to a muscarinic receptor on the surface of the cell.

2. A compound according to claim 1 wherein the reactive group bound to said omega carbon of said alkyl group is selected from the group consisting of an isothiocyanate, a thiocyanate, a fumaramate methyl, a carboxyl methyl, a p-azidophenylethyl, a p-isothiocyanato-phenylethyl, a p-(bromacetoamido)phenylethyl and a 3-iodo-4-azidophenylethyl.

3. A compound according to claim 1 wherein $R_2$ is selected from the group consisting of methyl, ethyl, propyl, isopropyl, butyl, sec-butyl, tert butyl, guanidine, formamidine and acetamidine.

4. A compound which comprises an epoxide of an anhydroecgonine ester having a formula:

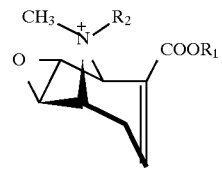

wherein $R_2$ is H, straight or branched $C_1$–$C_{10}$ alkyl or an amidine; and wherein $R_1$ is straight or branched $C_1$–$C_{10}$ alkyl, to the omega carbon of which is bound a reactive organic group capable of binding covalently to a constituent of the surface of a cell after said compound has bound to a muscarinic receptor on the surface of the cell.

5. A compound which comprises a substituted quaternary atropine having the chemical formula:

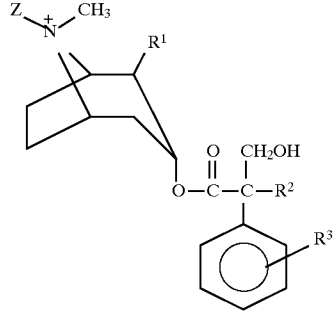

wherein Z is a straight or branched $C_1$–$C_{10}$ alkyl or an amidine; and at least one of $R^1$, $R^2$ and $R^3$ is a substituent selected from the group consisting of an isothiocyanate, a thiocyanate, a fumaramate methyl ester, a carboxyl methyl ester, a p-azidophenylethylester, a p-isothiocyanatophenylethylester, a p(bromacetoamido)phenylethylester and a 3-iodo-4-azidophenylethylester.

6. A compound which comprises a substituted quaternary atropine epoxide compound having the chemical formula

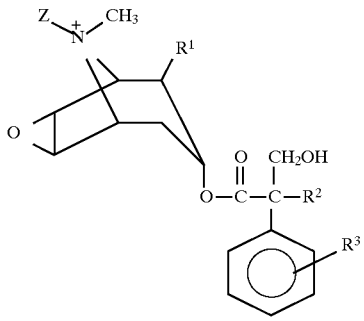

(a) wherein Z is a straight or branched chain $C_1$–$C_{10}$ alkyl or an amidine; and (b) at least one of $R^1$, $R^2$ and $R^3$ is a substituent selected from the group consisting of an isothiocyanate, a thiocyanate, a fumaramate methyl ester, a carboxyl methyl ester, a p-azidophenylethylester, a p-isothiocyanatophenylethylester, a p(bromacetoamido)phenylethylester and a 3-iodo-4-azidophenylethylester.

7. An irreversible antimuscarinic pharmaceutical composition comprising:
(a) an effective amount of a compound according to claim 1; and
(b) a pharmaceutically acceptable carrier or excipient.

8. An irreversible antimuscarinic pharmaceutical composition comprising:
(a) an effective amount of a compound according to claim 2; and
(b) a pharmaceutically acceptable carrier or excipient.

9. An irreversible antimuscarinic pharmaceutical composition comprising:
(a) an effective amount of a compound according to claim 3; and
(b) a pharmaceutically acceptable carrier or excipient.

10. An irreversible antimuscarinic pharmaceutical composition comprising:
(a) an effective amount of a compound according to claim 4; and
(b) a pharmaceutically acceptable carrier or excipient.

11. An irreversible antimuscarinic pharmaceutical composition comprising:
(a) an effective amount of a compound according to claim 5; and
(b) a pharmaceutically acceptable carrier or excipient.

12. An irreversible antimuscarinic pharmaceutical composition comprising:
(a) an effective amount of a compound according to claim 6; and
(b) a pharmaceutically acceptable carrier or excipient.

13. A method for preventing or inhibiting a muscarinic cholinergic response in a cell or tissue comprising providing to said cell or tissue an effective anticholinergic concentration of a compound according to claim 1.

14. A method for preventing or inhibiting a muscarinic cholinergic response in a cell or tissue comprising providing to said cell or tissue an effective anticholinergic concentration of a compound according to claim 2.

15. A method for preventing or inhibiting a muscarinic cholinergic response in a cell or tissue comprising providing to said cell or tissue an effective anticholinergic concentration of a compound according to claim 3.

16. A method for preventing or inhibiting a muscarinic cholinergic response in a cell or tissue comprising providing to said cell or tissue an effective anticholinergic concentration of a compound according to claim 4.

17. A method for preventing or inhibiting a muscarinic cholinergic response in a cell or tissue comprising providing to said cell or tissue an effective anticholinergic concentration of a compound according to claim 5.

18. A method for preventing or inhibiting a muscarinic cholinergic response in a cell or tissue comprising providing to said cell or tissue an effective anticholinergic concentration of a compound according to claim 6.

* * * * *